United States Patent
Hartley et al.

(10) Patent No.: US 6,939,370 B2
(45) Date of Patent: Sep. 6, 2005

(54) THORACIC AORTIC STENT GRAFT DEPLOYMENT DEVICE

(75) Inventors: David Ernest Hartley, Subiaco (AU); Leigh Anthony Huffer, Queensland (AU)

(73) Assignees: Cook Incorporated, Bloomington, IN (US); William Cook Europe ApS, Bjaeverskov (DK); William A. Cook Australia Pty. Ltd., Queensland (AU)

( * ) Notice: Subject to any disclaimer, the term of this patent is extended or adjusted under 35 U.S.C. 154(b) by 172 days.

(21) Appl. No.: 10/609,846

(22) Filed: Jun. 30, 2003

(65) Prior Publication Data

US 2004/0098079 A1 May 20, 2004

Related U.S. Application Data

(60) Provisional application No. 60/392,667, filed on Jun. 28, 2002.

(51) Int. Cl.[7] ................................................. A61F 2/06
(52) U.S. Cl. ..................... 623/1.11; 606/108; 606/198
(58) Field of Search ........................ 623/1.11; 606/198, 606/195, 191, 194, 108; 604/104

(56) References Cited

U.S. PATENT DOCUMENTS

| | | | | |
|---|---|---|---|---|
| 5,201,757 A | * | 4/1993 | Heyn et al. | 606/198 |
| 5,401,257 A | * | 3/1995 | Chevalier et al. | 604/265 |
| 5,403,341 A | * | 4/1995 | Solar | 606/198 |
| 5,415,664 A | * | 5/1995 | Pinchuk | 623/1.11 |
| 5,480,423 A | * | 1/1996 | Ravenscroft et al. | 623/1.11 |
| 5,693,083 A | * | 12/1997 | Baker et al. | 623/1.11 |
| 5,817,102 A | * | 10/1998 | Johnson et al. | 606/108 |

\* cited by examiner

*Primary Examiner*—Brian E Pellegram
*Assistant Examiner*—Christopher Prone
(74) *Attorney, Agent, or Firm*—Richard J. Godlewski

(57) ABSTRACT

A stent graft deployment device adapted for release of a distal end (29) of a stent graft (25) before the proximal end (27) of the stent graft (25). The arrangement (15) allows movement of at least part of the deployment catheter (23) independently of movement of a proximal end release mechanism has a fixed handle (16) associated with a trigger wire release mechanism (6) and a sliding handle (17) to which the deployment catheter and a capsule (21) are fixed. The sliding handle (17) is mounted on the fixed handle (16) and can slide longitudinally with respect to the fixed handle (16).

26 Claims, 6 Drawing Sheets

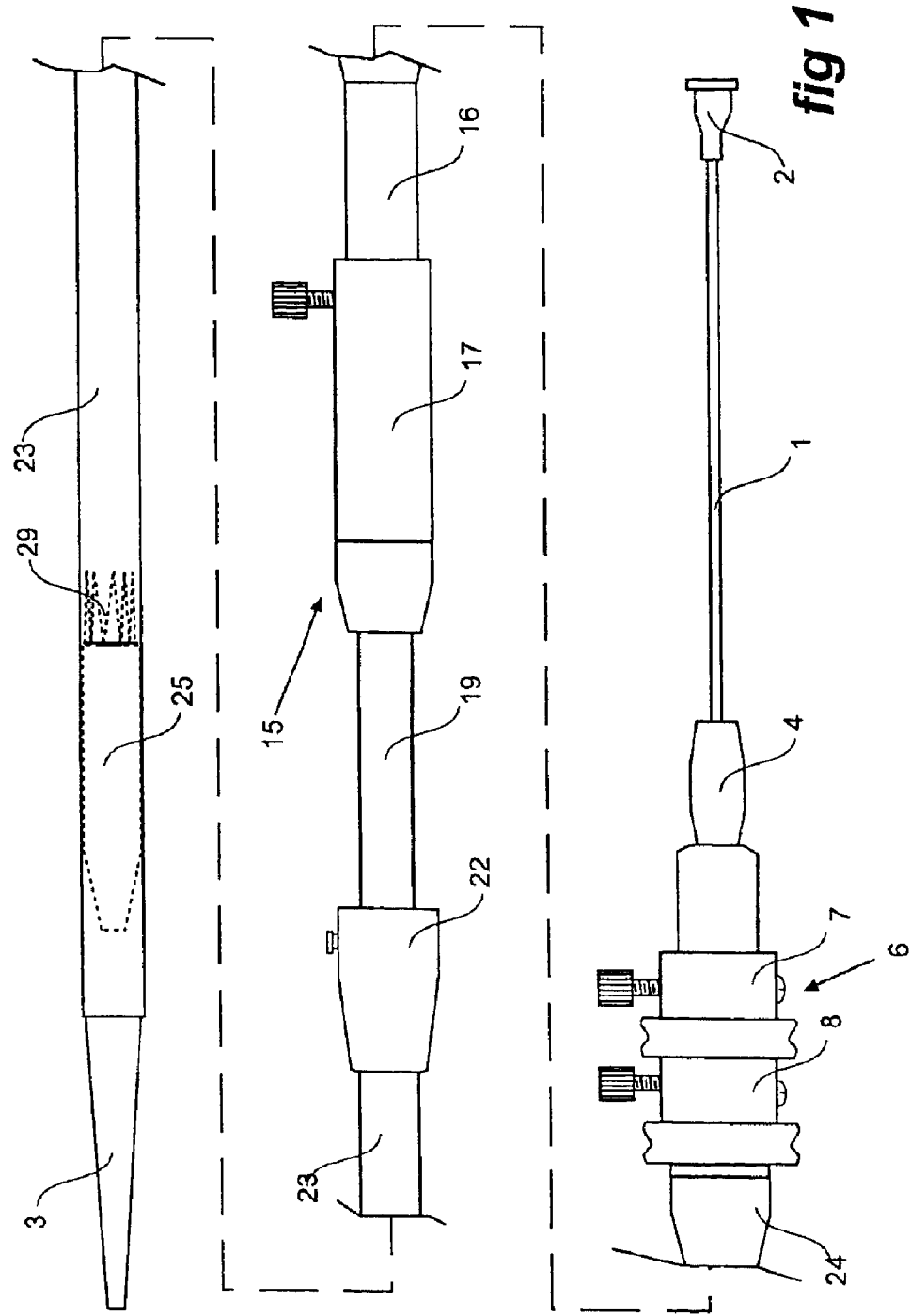

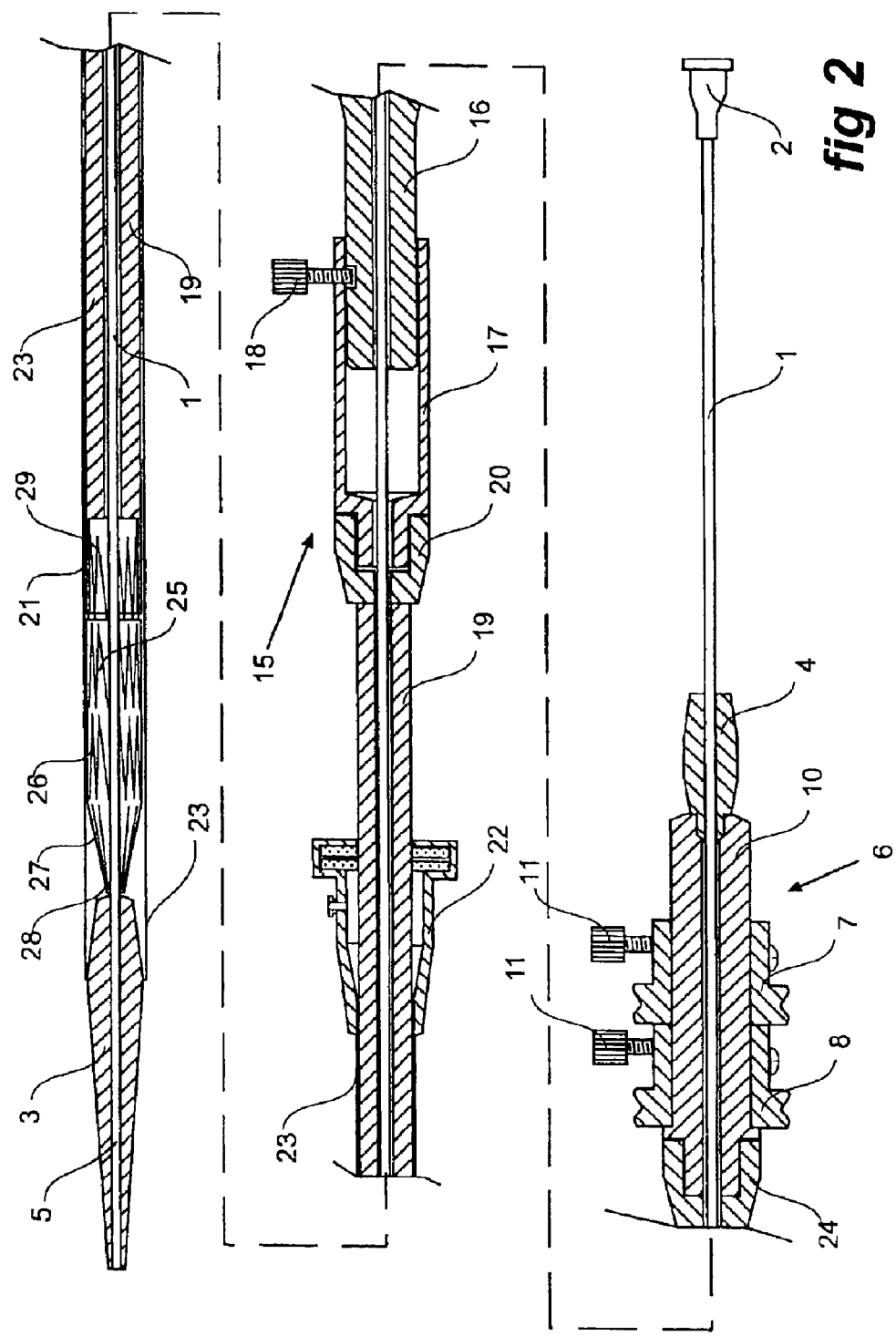

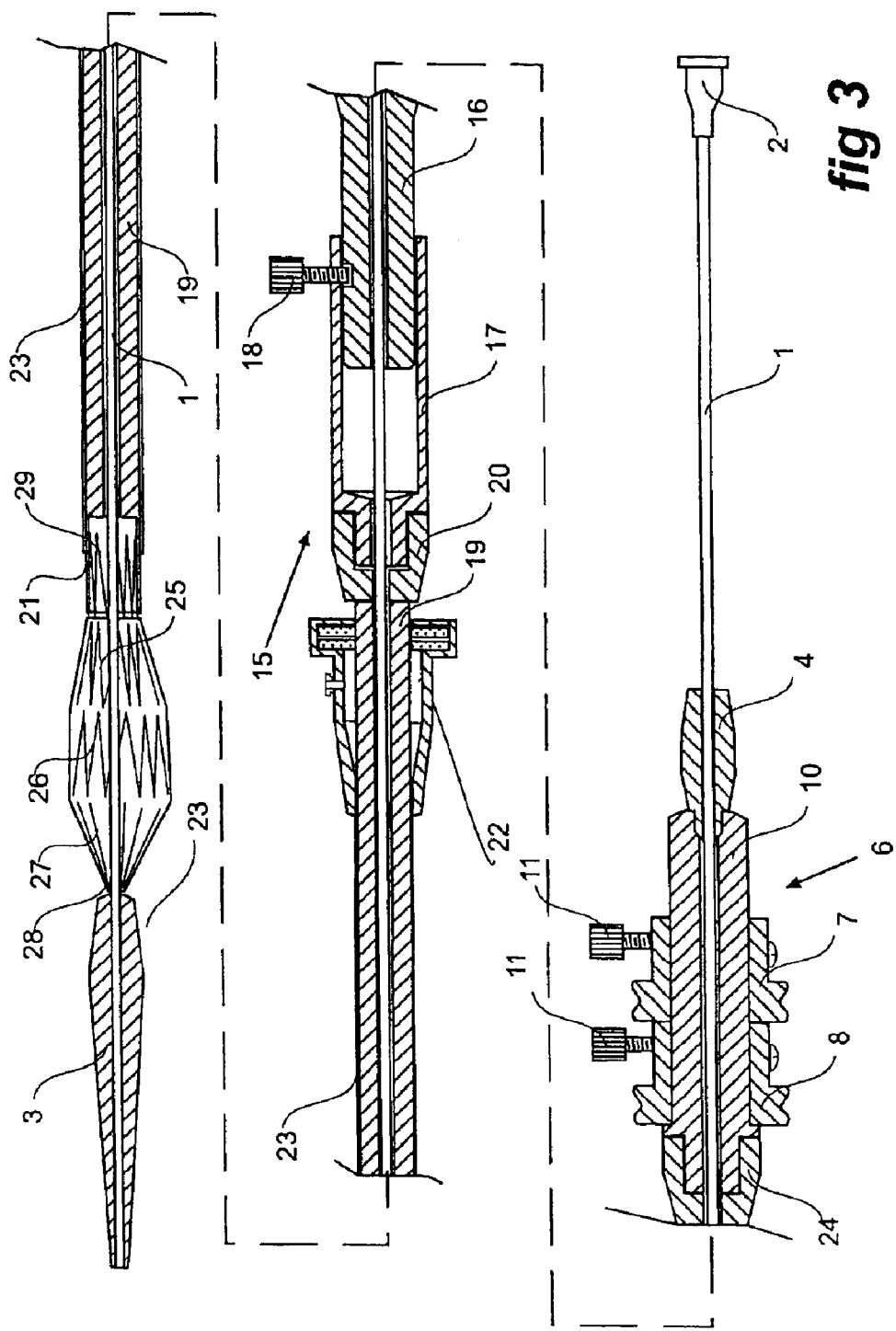

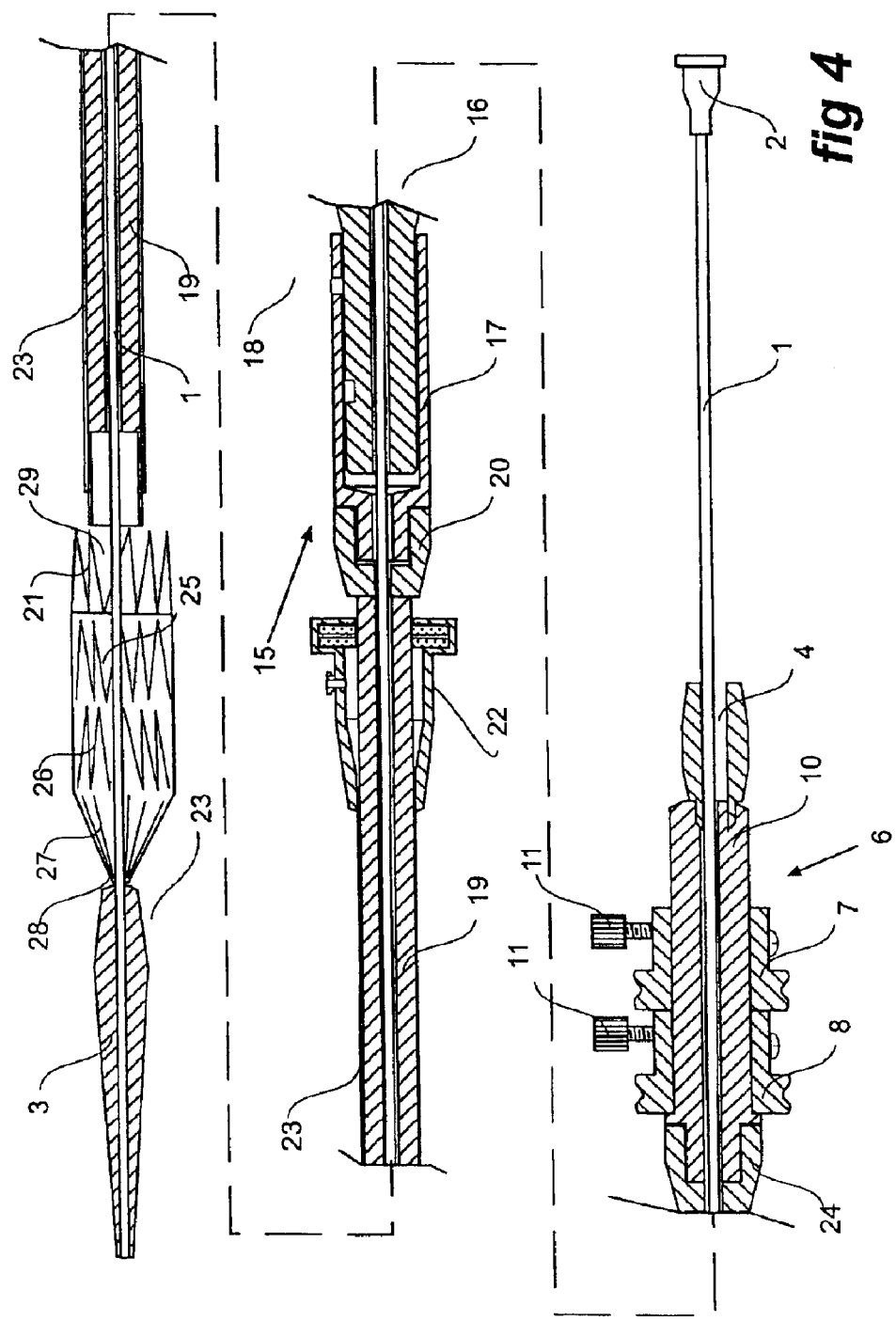

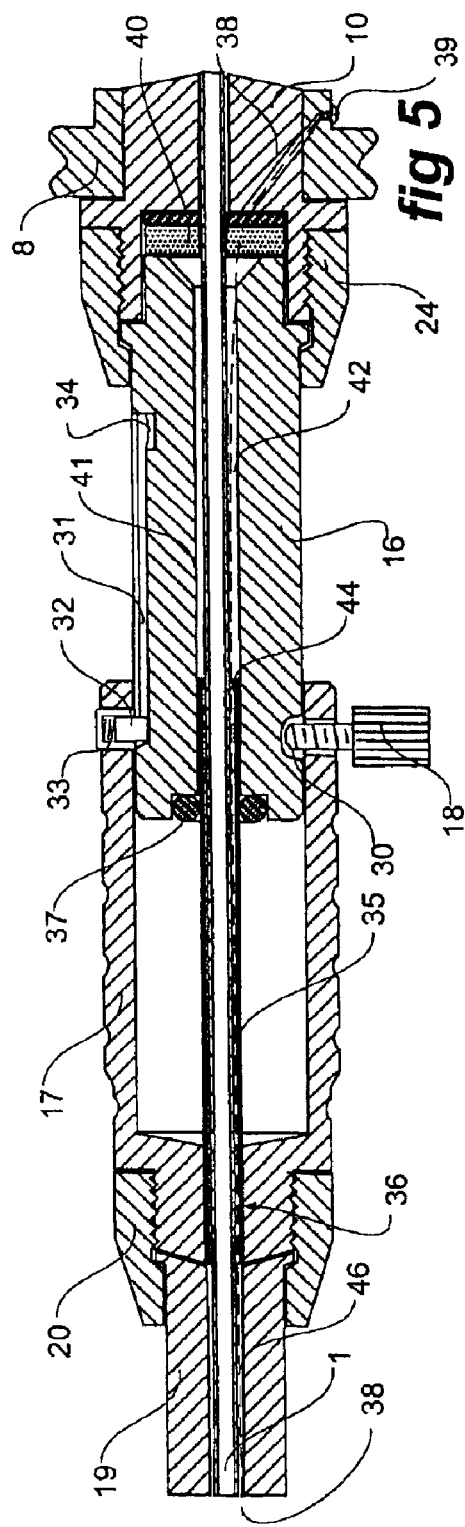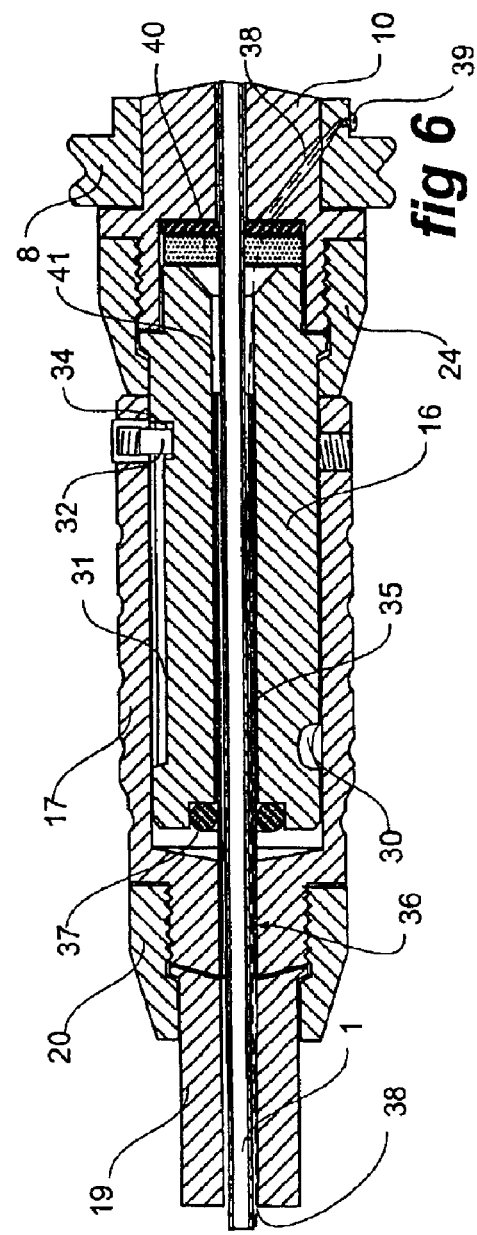

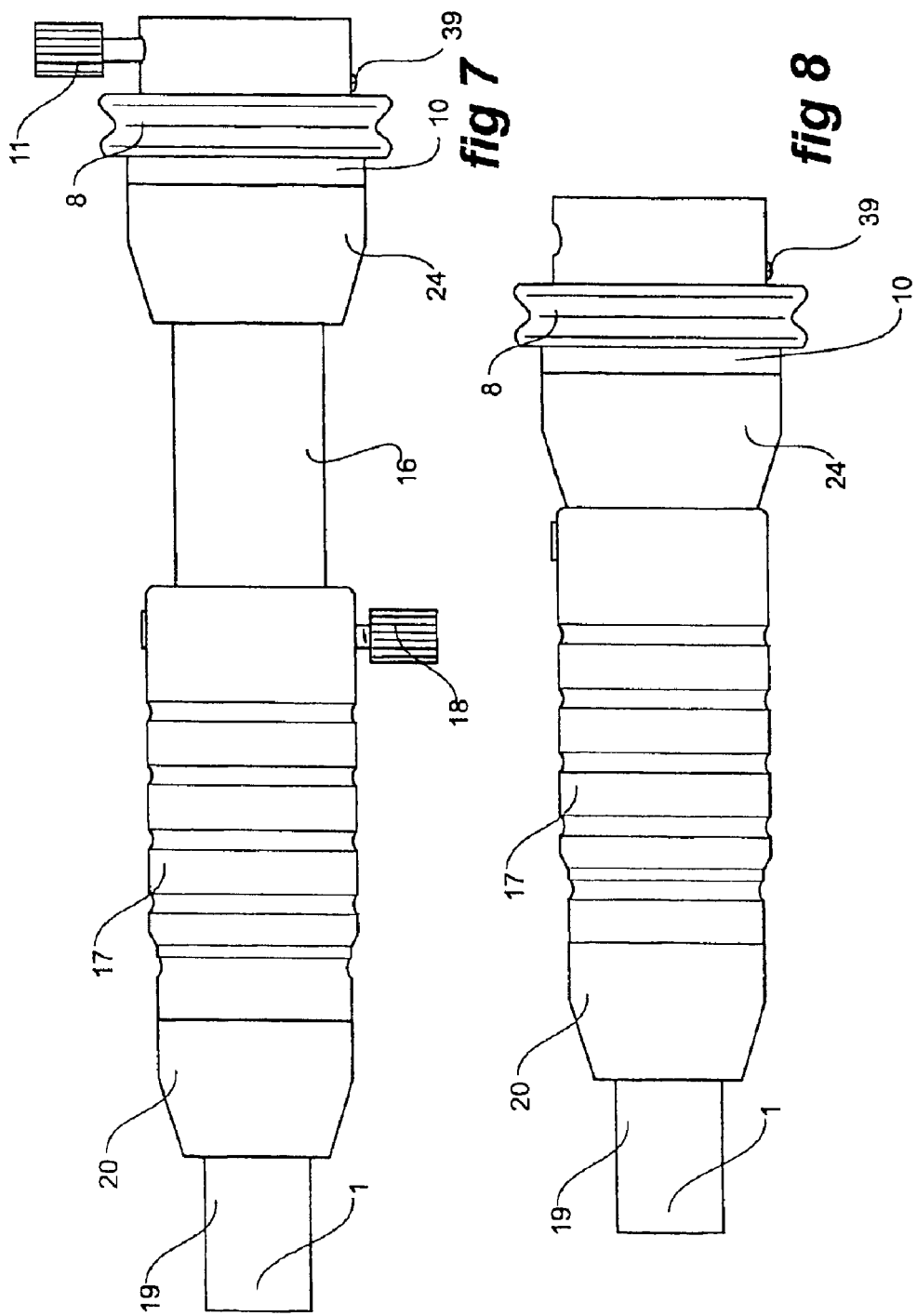

THORACIC AORTIC STENT GRAFT DEPLOYMENT DEVICE

CROSS-REFERENCE TO RELATED APPLICATIONS

This application claims priority to provisional application Ser. No. 60/392,667, filed Jun. 28, 2002. This application is also related to provisional application Ser. No. 60/391,737, filed Jun. 26, 2002, and entitled "Stent-Graft Fastening Arrangement."

TECHNICAL FIELD

This invention relates to a device for the deployment of a stent graft within the aorta and particularly in relation to deployment within the thoracic aorta.

BACKGROUND OF THE INVENTION

Throughout this specification when referring to deployment of a stent graft or prosthesis within the aorta of a patient the term proximal will be used for that end of both the deployment device and the stent graft at that end which is closer to the heart of a patient and the term distal will be used for that end of the deployment device or stent graft which in use is furthest from the heart. When applied to other vessels corresponding terms such as caudal and cranial should be understood.

Deployment of stent grafts within the thoracic aorta using an endovascular deployment method through the iliac arteries into the aorta can be done with a deployment device which has retained on it a stent graft which includes an exposed stent at the distal end of the graft.

As the stent graft has in one embodiment an exposed stent at the distal end preferably with barbs on it, it must be deployed in a device which keeps the barbs covered until deployment is required. This can be done with a capsule, which covers the exposed stent, but there is a problem. When withdrawing the capsule, a proximal end retention system, which uses trigger wires to retain the proximal end of the stent, can be released by pulling the trigger wires, thereby releasing part of the graft prematurely.

It is the object of this invention to provide a deployment device which overcomes this problem or at least provides the physician with a useful alternative device.

SUMMARY OF THE INVENTION

In one form therefore although this may not necessarily be the only or broadest form the invention is said to reside in a stent graft deployment device which holds a stent graft in a retained condition and is arranged to release a distal end of a stent graft before a proximal end of the stent graft, the device having a proximal stent graft end release mechanism and a distal stent graft end release mechanism associated with a deployment catheter and an arrangement to allow movement of at least part of the deployment catheter including the distal stent graft end release mechanism independent of movement of the proximal stent graft release mechanism.

It will be seen that by this method, movement of the deployment catheter, which enables release of the distal end of the stent graft, can be achieved without movement of the trigger wire release mechanism.

Preferably the deployment catheter includes a capsule engaging the distal end of the stent graft or prosthesis or a distally extending exposed stent on the stent graft or prosthesis.

The trigger wires may be used for both the proximal end and the distal end of the prosthesis or stent graft with separate trigger wire release mechanisms for each. The trigger wire release mechanism for the distal end is actuated before removing the distal exposed stent capsule.

There may be provided a sheath over the deployment catheter to cover the stent graft during initial deployment with the sheath manipulator fixed onto the deployment catheter. Movement of the sheath manipulator on the deployment catheter will move the sheath with respect to the deployment catheter and expose the stent graft.

The arrangement to allow movement of the deployment catheter independently of movement of the trigger wire release mechanism may include a fixed handle associated with the trigger wire release mechanism and to which the trigger wires are fixed and a sliding handle to which the deployment catheter and the capsule are fixed. The sliding handle is preferably mounted on the fixed handle and can slide with respect to it from a position where the capsule on the deployment catheter covers the exposed stents at the distal end of the stent graft to a position where the exposed stents are released. Hence moving the sliding handle with respect to the fixed handle moves the deployment catheter and the capsule without releasing the trigger wires for the proximal end of the stent graft.

There may be an arrangement which prevents movement of the sliding handle with respect to the moving handle until this movement is required. This arrangement may be provided by a thumbscrew fixed to the sliding handle which engages against a portion of the fixed handle to prevent inadvertent or early movement of the sliding handle with respect to the fixed handle. The thumbscrew is removed when it is desired to move the sliding handle.

There may also be provided a mechanism which prevents the deployment catheter from being moved forward after an initial movement back. Such a mechanism may be provided by a spring loaded pin or plunger mechanism on one of the handles which engages the other of the handles and allows movement from the position where the capsule on the deployment catheter is engaged onto the exposed stents to a position where the deployment catheter is disengaged and at that time the spring loaded pin mechanism engages a recess in the other handle portion to prevent forward movement again.

There may be provided a hemostatic seal associated with the sliding handle to prevent loss of blood through the sliding mechanism. The hemostatic seal may include a guide tube fixed onto the deployment catheter and sliding into a central lumen in the fixed handle with an O ring around it to seal.

The stages of operation of a deployment device are as follows. First once the deployment device is deployed in the correct position within the anatomy of the human or animal the sheath is withdrawn to expose the stent graft. At this stage the proximal end of the stent graft is retained by mooring loops actuated by a trigger wire and the distal end of the stent graft is retained by a capsule and a trigger wire.

In an alternative form the invention is said to reside in a stent graft deployment apparatus comprising a deployment catheter having a proximal end adapted to be introduced into a patient and a distal end adapted to remain outside a patient, the distal end including a handle arrangement, the catheter having at a proximal end thereof a region adapted in use to contain a stent graft; a sheath arrangement adapted in use to extend over and cover the region adapted to be moved with respect to the catheter to expose the region to thereby enable deployment of the stent graft; a nose cone dilator positioned at the proximal end of the deployment catheter; a distal retention arrangement for the stent graft at a distal end of the region and comprising a proximally facing capsule having a passageway and adapted to retain the distal end of a stent graft; the handle arrangement including a fixed handle and a sliding handle, at least the capsule being affixed to the sliding handle, whereby movement of the sliding handle with respect to the fixed handle moves the capsule independent of movement of the nose cone dilator.

In a further form the invention is said to reside in a stent graft deployment apparatus comprising a deployment catheter having a proximal end adapted to be introduced into a patient and a distal end adapted to remain outside a patient, the distal end including a handle arrangement; a longitudinal lumen through the deployment catheter; a guide wire catheter extending through the longitudinal lumen and extending proximally of the deployment catheter, the guide wire catheter having a proximal end and a distal end; and the guide wire catheter being movable longitudinally and rotationally with respect to the deployment catheter; a nose cone dilator being attached to proximal end of the guide wire catheter and extending proximally thereof; a sheath arrangement adapted in use to cover at least a portion of the deployment catheter and to extend to the nose cone dilator and adapted to be moved with respect to the catheter to enable deployment of a stent graft retained on the deployment device; a distal retention arrangement for the stent graft at a proximal end of the deployment catheter and comprising a proximally facing capsule having a passageway and adapted to retain a distal end of a stent graft; the handle arrangement including a fixed handle and a sliding handle, the deployment catheter and the capsule being affixed to the sliding handle, whereby movement of the sliding handle with respect to the fixed handle moves the deployment catheter and the capsule independent of movement of the nose cone dilator. Preferably there is a proximal retention arrangement on the guide wire catheter distal of the nose cone dilator for the proximal end of the stent graft and the proximal retention arrangement can include at least one proximal trigger wire. The proximal trigger wire can extend from the outside of the patient where it is retained by a trigger wire release mechanism on the fixed handle.

Preferably the distal retention arrangement includes an aperture extending through the capsule and a distal trigger wire extending along the deployment catheter and extendable through the aperture. The distal trigger wire can extend from the outside of the patient where it is retained by a trigger wire release mechanism on the fixed handle.

Preferably the sliding handle is mounted on the fixed handle and can slide longitudinally with respect to the fixed handle.

There can be further included a locking arrangement which prevents movement of the sliding handle with respect to the fixed handle. The locking arrangement can comprise a thumbscrew fixed to the sliding handle which engages against a portion of the fixed handle to prevent inadvertent or early movement of the sliding handle with respect to the fixed handle and wherein the thumbscrew can be removed when it is desired to move the sliding handle. There also can be a lock mechanism which prevents the sliding handle from being moved forward after an initial movement back. The lock mechanism can be provided by a spring loaded pin or plunger mechanism on one of the fixed handle or the sliding handle which engages the other of the fixed or sliding handles and allows movement of the deployment catheter from the position where the capsule on the deployment catheter is engaged onto the exposed stents to a position where the deployment catheter is disengaged and wherein at that time the spring loaded pin mechanism engages a recess in the other of the fixed or sliding handles to prevent further movement.

There can be further included a hemostatic seal associated with the fixed handle to prevent loss of blood between the fixed handle and the sliding handle. The hemostatic seal can include a guide tube fixed onto the deployment catheter and sliding into a central lumen in the fixed handle with an O-ring in the fixed handle engaging around the guide tube.

The stages of operation of deployment device are as follows. First once the deployment device is deployed in the correct position within the anatomy of the human or animal, the sheath is withdrawn to expose the stent graft. At this stage the proximal end of the stent graft is retained by mooring loops actuated by a trigger wire and the distal end of the stent graft is retained by a capsule and a trigger wire.

Next the distal trigger wire release mechanism is operated and the trigger wire release mechanism is completely withdrawn and discarded to remove the trigger wire from the distal end of the stent graft.

Next the thumbscrew on the sliding handle is released and discarded.

Next it is necessary to pull back on the deployment catheter manipulator so that the sliding handle moves with respect to the fixed handle until the spring pin engages into a recess in the fixed handle to withdraw the capsule from the distal end of the stent graft. At this stage the distal end of the stent graft is deployed. At this stage, too, the spring pin prevents any forward movement of the deployment catheter.

Next the proximal trigger wire release mechanism is withdrawn and discarded to remove the trigger wire from the proximal end of the stent graft. This releases the mooring loops and the graft is then fully deployed.

Finally the pin vice fixed to the fixed handle is released to withdraw the nose cone of the deployment device towards the capsule and then the deployment device is withdrawn.

Alternatively at this stage the sheath may be left in place and the deployment device less the sheath can be withdrawn so other devices such as an inflatable balloon to ensure complete engagement against the walls of the aorta may be deployed through the sheath.

BRIEF DESCRIPTION OF THE DRAWING

FIG. 1 shows a general external view of the deployment device according to one embodiment of this invention;

FIG. 2 shows a longitudinal cross-sectional view of the embodiment shown in FIG. 1;

FIG. 3 shows the same view as FIG. 2 but after withdrawal of the sheath;

FIG. 4 shows the same view as FIG. 3 but after activation of the sliding handle;

FIG. 5 shows a detailed longitudinal cross-sectional view of the sliding and fixed handle portion of one embodiment of a deployment device according to the invention;

FIG. 6 shows a view of the embodiment shown in FIG. 5 after withdrawal of the capsule;

FIG. 7 shows a side view of the embodiment shown in FIG. 5; and

FIG. 8 shows a side view of the embodiment shown in FIG. 6 after withdrawal of the capsule.

DETAILED DESCRIPTION

Now looking more closely at the drawings and in particular FIGS. 1 and 2, it will be seen that the deployment device generally comprises, working from the inside towards the outside, a guide wire catheter 1 which extends the full length of the device from a syringe socket 2 at the far distal end of the deployment device to a nose dilator 3 at the proximal end of the deployment device.

The nose cone dilator 3 is fixed to the guide wire catheter 1 and moves with it.

The nose cone dilator has a through bore 5 as an extension of the lumen of the guide wire catheter 1 so that the deployment device can be deployed over a guide wire (not shown).

To lock the guide wire catheter 1 with respect to the deployment device in general, a pin vice 4 is provided.

The trigger wire release mechanism generally shown as 6 at the distal end of the deployment device includes a distal end trigger wire release mechanism 7 and a proximal end trigger wire release mechanism 8. The trigger wire release mechanisms 7 and 8 slide on a portion of the fixed handle 10. Until such time as they are activated, the trigger wire mechanisms 7 and 8 which are fixed by thumbscrews 11 and remain fixed with respect to the fixed portion of the fixed handle.

Immediately proximal of the trigger wire release mechanism 6 is a sliding handle mechanism generally shown as 15. The sliding handle mechanism 15 generally includes a fixed handle extension 16 of the fixed handle 10 and a sliding portion 17. The sliding portion 17 slides over the fixed handle extension 16. A thumbscrew 18 fixes the sliding portion 17 with respect to the fixed portion 16.

The fixed handle portion 16 is affixed to the trigger wire mechanism handle 10 by a screw threaded nut 24.

The sliding portion of the handle 17 is fixed to the deployment catheter 19 by a mounting nut 20.

A deployment catheter extends from the sliding handle 17 through to a capsule 21 at the proximal end of the deployment catheter 19.

Over the deployment catheter 19 is a sheath manipulator 22 and a sheath 23, which slides with respect to the deployment catheter 19 and in the ready to deploy situation as shown in FIGS. 1 and 2 extends from the sheath manipulator 22 forward to the nose cone dilator 3 to cover a stent graft 25 retained on the deployment device distally of the nose cone dilator 3.

In the ready to deploy condition shown in FIGS. 1 and 2, the sheath 23 assists in retaining the stent graft 25, which includes self-expanding stents 26 in a compressed condition. The proximal covered stent 27 is retained by a fastening at 28 which is locked by a trigger wire (not shown) which extends to trigger wire release mechanism 8. The distal exposed stent 29 on the stent graft 25 is retained within the capsule 21 on the deployment catheter 19 and is prevented from being released from the capsule by a distal trigger wire (not shown) which extends to the distal trigger wire release mechanism 7.

FIG. 3 shows the same view as FIG. 2 but after withdrawal of sheath 23, and FIG. 4 shows the same view as FIG. 3, but after activation of sliding handle mechanism 15.

In FIG. 3, the sheath manipulator 22 has been moved distally so that its proximal end clears the stent graft 25 and lies over the capsule 21. Freed of constraint, the self expanding stents 26 of the stent graft 25 are able to expand. However, the fastening 28 still retains the proximal end of the proximal stent 27, and the capsule 21 still retains the distally extending exposed stent 29. At this stage, the proximal and distal ends of the stent graft 25 can be independently repositioned, although if the proximal stent 27 included barbs as it has in some embodiments, the proximal end can only be moved proximally.

Once repositioning has been done, the distal end of the stent graft 25 should be released first. This is done so that blood flow, which is from proximal to distal, cannot inflate the stent graft in a wind sock type of effect and cause migration of the stent graft during deployment. For this reason, it is desirable to release the distal end of the stent graft first, but if the capsule is moved distally, then the release mechanisms could also move, which could release the proximal end prematurely. Hence the distal trigger wire release mechanism 7 on the handle 10 is removed to withdraw the distal trigger wire. Then the thumb screw 18 is removed, and the sliding handle 17 is moved distally to the position shown in FIG. 4. This moves the capsule 21 to release the exposed stent 29. As the fastening 28 is retained on the guide wire catheter 1, just distal of the nose cone dilator 3 and the guide wire catheter 1 is locked in position on the handle 10 by pin vice 4, then the proximal trigger wire release mechanism 8, which is on the handle 10, does not move when moving the sliding handle, deployment catheter 19 and capsule 21 so the proximal end of the stent graft 25 remains in a retained position. The proximal end of the stent graft 25 can be again manipulated at this stage by manipulation of the handle. Although if the proximal stent 27 included barbs as discussed above, the proximal end can only be moved proximally. The proximal fastening 28 can then be released by removal of the proximal trigger wire release mechanism 8.

Now looking more closely at FIGS. 5 to 8, the detailed construction of a particular embodiment of a sliding handle mechanism according to this invention is shown. FIGS. 5 and 7 show the sliding handle mechanism in the ready to deploy condition. FIGS. 6 and 8 show the mechanism when the deployment catheter and hence the capsule has been withdrawn by moving the sliding handle with respect to the fixed handle.

The fixed handle extension 16 is joined to the trigger wire mechanism handle 10 by screw threaded nut 24.

The sliding handle 17 is fixed to the deployment catheter 19 by screw threaded fixing nut 20 so that the deployment catheter moves along with the sliding handle 17. The sliding handle 17 fits over the fixed handle extension 16 and, in the ready to deploy situation, is fixed in relation to the fixed handle by locking thumbscrew 18, which engages into a recess 30 in the fixed handle extension 16. On the opposite side of the fixed handle extension 16 is a longitudinal track 31 into which a plunger pin 32 spring loaded by means of spring 33 is engaged. At the distal end of the track 31 is a recess 34.

A guide tube 35 is fixed into the proximal end of the sliding handle 17 at 36 and extends back to engage into a central lumen 41 in the fixed handle extension 16 but able to move in the central lumen 41. An O ring 37 seals between the fixed handle extension 16 and guide tube 35. This provides a hemostatic seal for the sliding handle mechanism. The trigger wire 38, which is fixed to the trigger wire releasing mechanism 8 by means of screw 39, passes through the annular recess 42 between the fixed handle extension 16 and the guide wire catheter 1 and then more proximally in the annular recess 44 between the guide wire catheter 1 and the guide tube 35 and forward to extend through the annular recess 46 between the guide wire catheter 1 and the deployment catheter 19 and continues forward to the proximal retaining arrangement. Similarly the distal trigger wire (not shown) extends to the distal retaining arrangement.

A further hemostatic seal 40 is provided where the guide wire catheter 1 enters the trigger wire mechanism handle 10 and the trigger wires 38 pass through the hemostatic seal 40 to ensure a good blood seal.

As can be seen in FIGS. 6 and 8, the locking thumbscrew 18 has been removed and discarded, and as the sliding handle is moved onto the fixed handle, the plunger pin 32 has slid back along the track 31 to engage into the recess 34. At this stage, the sliding handle cannot be moved forward again.

As the trigger wire release mechanisms 7 and 8 are on the trigger wire mechanism handle 10, which is fixed with respect to the fixed handle 16, then the proximal trigger wire 38 is not moved when the deployment catheter 19 and the sliding handle 17 is moved so that it remains in position and does not prematurely disengage.

Throughout this specification various indications have been given as to the scope of this invention but the invention is not limited to any one of these but may reside in two or more of these combined together. The examples are given for illustration only and not for limitation.

Throughout this specification unless the context requires otherwise the words comprise and include and variations such as comprising and including will be understood to imply the inclusion of a stated integer or group of integers but not the exclusion of any other integer or group of integers.

What is claimed is:

1. A stent graft deployment device which holds a stent graft in a retained condition and arranged to release of a distal end of a stent graft before the proximal end of the stent graft, the device having a proximal stent graft end release mechanism and a distal stent graft end release mechanism associated with a deployment catheter and an arrangement to allow movement of at least part of the deployment catheter including the distal stent graft end release mechanism independent of movement of the proximal stent graft end release mechanism wherein the distal end release mechanism associated with the deployment catheter includes a capsule for engaging the distal end of the stent graft or a distally extending exposed stent on the stent graft and the arrangement to allow movement of at least part of the deployment catheter independently of movement of the proximal end release mechanism includes a fixed handle associated with a trigger wire release mechanism and a sliding handle to which the deployment catheter and the capsule are fixed.

2. A stent graft deployment device as in claim 1 wherein the proximal end release mechanism includes at least one proximal trigger wire.

3. A stent graft deployment device as in claim 1 wherein the distal end release mechanism includes a distal trigger wire.

4. A stent graft deployment device as in claim 3 including an arrangement to remove the distal trigger wire at the distal end of the stent graft before removing the distal exposed stent capsule.

5. A stent graft deployment device as in claim 1 further including a sheath over the deployment catheter to cover the stent graft during initial deployment with the sheath being actuatable by a sheath manipulator slidably received onto the deployment catheter and wherein movement of the sheath manipulator on the deployment catheter will move the sheath with respect to the deployment catheter to expose the stent graft.

6. A stent graft deployment device as in claim 1 wherein the sliding handle is mounted on the fixed handle and can slide longitudinally with respect to the fixed handle.

7. A stent graft deployment device as in claim 1 further including a locking arrangement which prevents movement of the sliding handle with respect to the fixed handle.

8. A stent graft deployment device as in claim 7 wherein the locking arrangement comprises a thumbscrew fixed to the sliding handle which engages against a portion of the fixed handle to prevent inadvertent or early movement of the sliding handle with respect to the fixed handle and wherein the thumbscrew can be removed when it is desired to move the sliding handle.

9. A stent graft deployment device as in claim 1 further including a lock mechanism which prevents the sliding handle from being moved forward after an initial movement back.

10. A stent graft deployment device as in claim 9 wherein the lock mechanism is provided by a spring loaded pin or plunger mechanism on one of the fixed handle or the sliding handle which engages the other of the fixed or sliding handles and allows movement of the deployment catheter from the position where the capsule on the deployment catheter is engaged onto the exposed stents to a position where the deployment catheter is disengaged and wherein at that time the spring loaded pin mechanism engages a recess in the other of the fixed or sliding handles to prevent further movement.

11. A stent graft deployment device as in claim 1 further including a hemostatic seal associated with the fixed handle to prevent loss of blood between the fixed handle and the sliding handle.

12. A stent graft deployment device as in claim 11 wherein the hemostatic seal includes a guide tube fixed onto the deployment catheter and sliding into a central lumen in the fixed handle with an O-ring in the fixed handle engaging around the guide tube.

13. A stent graft deployment apparatus comprising:
a deployment catheter having a proximal end adapted to be introduced into
a patient and a distal end adapted to remain outside a patient, the distal end including a handle arrangement, the catheter having at a proximal end thereof a region adapted in use to contain a stent graft;
a sheath arrangement adapted in use to extend over and cover the region adapted to be moved with respect to the catheter to expose the region to thereby enable deployment of the stent graft;
a nose cone dilator positioned at the proximal end of the deployment catheter;
a distal retention arrangement for the stent graft at a distal end of the region and comprising a proximally facing capsule having a passageway and adapted to retain the distal end of a stent graft;
the handle arrangement including a fixed handle and a sliding handle, at least the capsule being affixed to the sliding handle, whereby movement of the sliding handle with respect to the fixed handle moves the capsule independent of movement of the nose cone dilator.

14. A stent graft deployment apparatus comprising:
a deployment catheter having a proximal end adapted to be introduced into a patient and a distal end adapted to remain outside a patient, the distal end including a handle arrangement;
a longitudinal lumen through the deployment catheter;
a guide wire catheter extending through the longitudinal lumen and extending proximally of the deployment catheter, the guide wire catheter having a proximal end and a distal end; and the guide wire catheter being movable longitudinally and rotationally with respect to the deployment catheter;

a nose cone dilator being attached to a proximal end of the guide wire catheter and extending proximally thereof;

a sheath arrangement adapted in use to cover at least a portion of the deployment catheter and to extend to the nose cone dilator and adapted to be moved with respect to the catheter to enable deployment of a stent graft retained on the deployment device;

a distal retention arrangement for the stent graft at a proximal end of the deployment catheter and comprising a proximally facing capsule having a passageway and adapted to retain a distal end of a stent graft;

the handle arrangement including a fixed handle and a sliding handle, the deployment catheter and the capsule being affixed to the sliding handle, whereby movement of the sliding handle with respect to the fixed handle moves the deployment catheter and the capsule independent of movement of the nose cone dilator.

15. A stent graft deployment apparatus as in claim 14 including a proximal retention arrangement on the guide wire catheter distal of the nose cone dilator for the proximal end of the stent graft.

16. A stent graft deployment apparatus as in claim 15 wherein the proximal retention arrangement includes at least one proximal trigger wire.

17. A stent graft deployment apparatus as in claim 16 wherein the proximal trigger wire extends from the outside of the patient where it is retained by a trigger wire release mechanism on the fixed handle.

18. A stent graft deployment apparatus as in claim 14 wherein the distal retention arrangement includes an aperture extending through the capsule and a distal trigger wire extending along the deployment catheter and extendable through the aperture.

19. A stent graft deployment apparatus as in claim 18 the distal trigger wire extends from the outside of the patient where it is retained by a trigger wire release mechanism on the fixed handle.

20. A stent graft deployment device as in claim 14 wherein the sliding handle is mounted on the fixed handle and can slide longitudinally with respect to the fixed handle.

21. A stent graft deployment device as in claim 20 further including a locking arrangement which prevents movement of the sliding handle with respect to the fixed handle.

22. A stent graft deployment device as in claim 21 wherein the locking arrangement comprises a thumbscrew fixed to the sliding handle which engages against a portion of the fixed handle to prevent inadvertent or early movement of the sliding handle with respect to the fixed handle and wherein the thumbscrew can be removed when it is desired to move the sliding handle.

23. A stent graft deployment device as in claim 14 further including a lock mechanism which prevents the sliding handle from being moved forward after an initial movement back.

24. A stent graft deployment device as in claim 23 wherein the lock mechanism is provided by a spring loaded pin or plunger mechanism on one of the fixed handle or the sliding handle which engages the other of the fixed or sliding handles and allows movement of the deployment catheter from the position where the capsule on the deployment catheter is engaged onto the exposed stents to a position where the deployment catheter is disengaged and wherein at that time the spring loaded pin mechanism engages a recess in the other of the fixed and sliding handles to prevent further movement.

25. A stent graft deployment device as in claim 14 further including a hemostatic seal associated with the fixed handle to prevent loss of blood between the fixed handle and the sliding handle.

26. A stent graft deployment device as in claim 25 wherein the hemostatic seal includes a guide tube fixed onto the deployment catheter and sliding into a central lumen in the fixed handle with an O-ring in the fixed handle engaging around the guide tube.

* * * * *